US006995236B2

(12) United States Patent
Kobayashi et al.

(10) Patent No.: US 6,995,236 B2
(45) Date of Patent: Feb. 7, 2006

(54) SPHINGOMYELIN DETECTING PROBE

(75) Inventors: Toshihide Kobayashi, Tokyo (JP); Etsuko Kiyokawa, Wako (JP); Akiko Hasegawa, Tokyo (JP)

(73) Assignee: Riken, Saitama (JP)

( * ) Notice: Subject to any disclaimer, the term of this patent is extended or adjusted under 35 U.S.C. 154(b) by 230 days.

(21) Appl. No.: 10/138,634

(22) Filed: May 6, 2002

(65) Prior Publication Data

US 2002/0168725 A1    Nov. 14, 2002

(30) Foreign Application Priority Data

May 8, 2001   (JP)   ............................. 2001-137087
Aug. 30, 2001 (JP)   ............................. 2001-261158

(51) Int. Cl.
    A61K 2/00    (2006.01)
    C12N 15/09   (2006.01)
    C12N 7/00    (2006.01)
(52) U.S. Cl. ...................... 530/300; 530/350; 530/314; 530/315; 530/316; 435/235.1; 435/320.1
(58) Field of Classification Search ................ 530/350, 530/300, 314, 315, 316; 435/320.1, 235.1
    See application file for complete search history.

(56) References Cited

U.S. PATENT DOCUMENTS

| 4,686,191 A   | 8/1987  | Itoh et al. |
| 4,939,094 A   | 7/1990  | Kuga et al. |
| 5,160,735 A   | 11/1992 | Yasumura et al. |
| 6,569,464 B1 * | 5/2003  | Mukherjee et al. ......... 424/520 |

FOREIGN PATENT DOCUMENTS

| JP | 58110600 | 7/1983 |
| JP | 2-227075 | 9/1990 |
| JP | 3-22979  | 1/1991 |

OTHER PUBLICATIONS

J. Rudinger. Characteristics of the amino acids as components of a peptide hormone sequence. In Peptide Hormones, JA Parsons, Ed. (1976) University Press, Baltimore. 2-7.*
SIGMA. Designing Custom Peptides. http://www.sigma-genosys.com/peptide_design.asp (Accessed Dec. 16, 2004). 2 pages.*
HJC Berendsen. A Glimpse of the Holy Grail? Science (1998) 282.642-643.*
D Voet and JG Voet. Biochemistry, 2nd Edition.(1995). 235-241.*
Toshihide Kobayashi et al., "Lysenin: Sphingomyelin Specific Probe", Molecular Biology of the Cell, vol. 11, pp. 314A (2000).
Yoshiyuki Sekizawa et al., "Molecular Cloning of cDNA for Lysenin, A Novel Protein in the Earthworm *Eisenia Foetida* that Causes Contraction of Rat Vascular Smooth Muscle", Gene, vol. 191, pp. 97-102 (1997).
Akiko Yamaji et al., "Lysenin, A Novel Sphingomyelin-Specific Binding Protein", The Journal of Biological Chemistry, vol. 273, No. 9, pp. 5300-5306 (1998).
K. Itoh et al., "Lysenin-Sphingomyelin Bindingon Cell Surface Increases During Oligodendrocyte Lineage In Vitro", Society for Neuroscience Abstracts, vol., 26, No. 1-2, pp. 601.3 (2000).
Masao Iwamori et al., "Sensitive Method for the Determination of Pulmonary Surfactant Phospholipid/Sphingomyelin Ratio in Human Amniotic Fluids for the Diagnosis fo Respiratory Distress Syndrome by thin-Layer Chromatography-Immunostaining", Analytical Biochemistry, vol. 238, pp. 29-33 (1996).
Josè A. Encinar et al., "Enzymatic Determination of Phosphatidylcholine, Sphingomyelin and Phosphatidylglycerol in Lipid Dispersions, Blood Cell Membranes and Rat Pulmonary Surfactant')", Eur. J. Chem Clin Biochem, vol. 34, pp. 9-15 (1996).
English Language Abstract of JP 58-110600.
Nishi et al., Agric. Biol. Chem., vol. 48, No. 3, pp. 669-6750 (1984).
Miyaji et al., Agric. Biol. Chem., vol. 53, No. 1, pp. 277-279 (1989).
Sekine et al., Proc. Natl. Acad. Sci., vol. 82, pp. 4306-4310 (1985).
Yanisch-Perron et al., Gene, vol. 33, pp. 103-119 (1985).
English Language Abstract of JP 3-22979.
Miyaji et al., Cytotechnology, vol. 3, pp. 133-140 (1990).
English Language Abstract of JP 2-227075.
Seed, B., Nature, vol. 329, pp. 840-842 (1987).
Mizukami et al., J. Biochem., vol. 101, pp. 1307-1310 (1987).
Nishibayashi et al., Plant Cell Reports, vol. 15, pp. 809-814 (1996).
Jefferson et al., The EMBO J., vol. 6, No. 13, pp. 3901-3907 (1987).
Terada et al., Mol. Gen. Genet., vol. 220, pp. 389-392 (1990).

(Continued)

Primary Examiner—Bruce R. Campell
Assistant Examiner—Andrew D. Kosar
(74) Attorney, Agent, or Firm—Greenblum & Bernstein, P.L.C.

(57) ABSTRACT

An object of the present invention is to provide a protein useful as a sphingomyelin detecting probe, which specifically recognizes sphingomyelin and has low cytotoxicity. The present invention provides a protein which has an amino acid sequence having, as the amino acid sequence from the 1st to the 48th amino acid, the amino acid sequence from the 1st to the 48th amino acid in Lysenin 1, and as the amino acid sequence from the 49th to the 298th amino acid, the amino acid sequence from the 51st to the 300th amino acid in Lysenin 3; and a protein which is obtained by deleting N terminal and/or C terminal from earthworm toxins Lysenin 1 or 3, and which specifically recognizes sphingomyelin.

8 Claims, 7 Drawing Sheets

OTHER PUBLICATIONS

Sekizawa et al., Gene, vol. 191, pp. 97-102 (1997).
Maguy Lassegues et al., "Sequence and Expression of an *Eisenia-fetida*-derived cDNA Clone that Encodes the 40-kDa Fetidin Antibacterial Protein", Eur. J. Biochem., vol. 246, pp. 756-762 (1997).

* cited by examiner

SPHINGOMYELIN DETECTING PROBE

TECHNICAL FIELD

The present invention relates to novel proteins which are useful as a sphingomyelin detecting probe. More particularly, the present invention relates to a chimera protein comprising Lysenin 1 and Lysenin 3 and a protein of partial amino acid sequence of Lysenin 1 or Lysenin 3, both of which specifically recognize sphingomyelin and have low cytotoxicity. The present invention relates to a gene which encodes said protein, a vector having said gene, a transformant having said vector, a reagent for detecting sphingomyelin comprising said protein, a method for detecting sphingomyelin using said protein, and a kit for detecting sphingomyelin.

BACKGROUND TECHNIQUE

Major lipid components in cell membrane include glycerolipid, sphingolipid, and cholesterol. Glycerolipid in animal cells has a structure in which 2 molecules of a fatty acid and a phosphate group are bound to a glycerol skeleton, and has, upon dispersion in an aqueous solution, a two layered membrane structure in which a hydrophobic fatty acid residue is present inside and a phosphate group portion is present outside. The formed two layered membrane structure has a property of liquid crystalline, and in 1972 Singer and Nicolson (United States) proposed a "fluid mosaic model" in which a protein is floating in such liquid crystal.

In addition to the cell membrane for separating the cell from outside, the cell also has a complicated membrane structure inside and has organelles having their own respective characteristic functions. A portion which constitutes a cell membrane is synthesized by an organelle referred to as an "endoplasmic reticulum" and is finally transported to a cell membrane through a Golgi apparatus.

Glycerolipid which is one component of a cell membrane, contains a fatty acid and a phosphate group. However, the types of fatty acid are various, and the phosphate group portion also has variety, for example, it may contain choline, ethanolamine, serine, or inositol. Further, sphingolipid to which a variety of saccharides such as glucose, galactose, or lactose are bound, exists. There are several tens of thousands of lipid molecules in the natural world if all the above lipids are included. The composition of the lipid varies depending on the type of organisms, the type of organs, the type of cells, and the type of organelles. Furthermore, the lipid composition of the inner layer constituting the lipid bilayer of the biomembrane is different from that of the outer layer.

Unlike glycerolipid, since sphingolipid has a base referred to as "sphingosine" as a skeleton, it can be either donor or acceptor of a hydrogen bond. Also, in general, sphingolipid binds to a long-chained fatty acid. Due to this structural character of sphingolipid, in the case of a plurality of sphingolipids, the hydrophilic portions are likely to aggregate through hydrogen bonding while the hydrophobic portions are likely to aggregate through the hydrophobic interaction of fatty acid chains. Simons et al. (Germany) proposed that sphingolipids on the cell membrane aggregate and form a lipid domain. They named this a "lipid raft" (hereinafter merely referred to as a "raft").

Ever since the concept of the "raft" as described above was proposed, it has been suggested that the raft plays an important role in the signal transduction, as well as cell adhesion, infection of viruses and bacteria, polymer translocation in the cell, and the like. In recent years, it has been shown that among sphingolipids, sphingomyelin is a necessary and enough factor in the formation of the raft.

The present inventors have heretofore found that Lysenin, which is a toxic protein secreted by *Eisenia foetida*, specifically binds to sphingomyelin.

Lysenin is already known and the existence of three types of Lysenin 1, 2, and 3 is known. Lysenin 1 is composed of 297 amino acid residues, and Lysenins 2 and 3 are composed of 300 amino acid residues. Among these, Lysenins 1 and 3 have high cytotoxicity and, thus, they could not be used for labeling sphingomyelin in living cells. Lysenin 2 does not recognize sphingomyelin. Therefore, Lysenins which have been heretofore reported, could not be put to practical use as sphingomyelin detecting probes.

DISCLOSURE OF THE INVENTION

Accordingly, an object of the present invention is to provide a protein useful as a sphingomyelin detecting probe, which specifically recognizes sphingomyelin and has low cytotoxicity. Another object of the present invention is to provide a gene coding for the protein, a vector having the gene, a transformant having the vector, a reagent for detecting sphingomyelin which comprises the protein, a method for detecting sphingomyelin using the protein, and a kit for detecting sphingomyelin.

The present inventors have conducted concentrated studies in order to achieve the above objects, and as a result, they have succeeded in obtaining a protein which has low toxicity and specifically recognizes sphingomyelin from Lysenin variants, thereby completing the present invention.

Thus, the present invention provides a protein having either of the following amino acid sequences:

(1) an amino acid sequence having, as the amino acid sequence from the 1st to the 48th amino acid, the amino acid sequence from the 1st to the 48th amino acid in Lysenin 1, and as the amino acid sequence from the 49th to the 298th amino acid, the amino acid sequence from the 51st to the 300th amino acid in Lysenin 3; or (2) an amino acid sequence derived from the amino acid sequence according to (1) above by substitution, deletion, and/or addition of one or more amino acids, which specifically recognizes sphingomyelin and has low cytotoxicity.

Another aspect of the present invention provides a protein having either of the following amino acid sequences:

(1) the amino acid sequence of SEQ ID NO: 3; or (2) an amino acid sequence derived from the amino acid sequence of SEQ ID NO: 3 by substitution, deletion, and/or addition of one or more amino acids, which specifically recognizes sphingomyelin and has low cytotoxicity.

A further aspect of the present invention provides a protein which is obtained by deleting N terminal and/or C terminal from earthworm toxins Lysenin 1 or 3, and which specifically recognizes sphingomyelin. Preferably, there is provided a protein obtained by deleting 50 to 200 amino acid residues of N terminal and/or C terminal of earthworm toxins Lysenin 1 or 3.

A further aspect of the present invention provides a protein having either of the following amino acid sequences:

(1) the amino acid sequence of SEQ ID NO: 5; or (2) an amino acid sequence derived from the amino acid sequence of SEQ ID NO: 5 by substitution, deletion, and/or addition of one or more amino acids, which specifically recognizes sphingomyelin and has low cytotoxicity.

A further aspect of the present invention provides a gene which encodes the above proteins of the present invention.

A still further aspect of the present invention provides a gene having either of the following nucleotide sequences:
 (1) the nucleotide sequence of SEQ ID NO: 4; or
 (2) a nucleotide sequence derived from the nucleotide sequence of SEQ ID NO: 4 by substitution, deletion, and/or addition of one or more nucleotides, which encodes a protein which specifically recognizes sphingomyelin and has low cytotoxicity.

A still further aspect of the present invention provides a gene having either of the following nucleotide sequences:
 (1) the nucleotide sequence of SEQ ID NO: 6; or
 (2) a nucleotide sequence derived from the nucleotide sequence of SEQ ID NO: 6 by substitution, deletion, and/or addition of one or more nucleotides, which encodes a protein which specifically recognizes sphingomyelin and has low cytotoxicity.

A still further aspect of the present invention provides a vector having the gene of the present invention.

A still further aspect of the present invention provides a transformant having the vector of the present invention.

A still further aspect of the present invention provides a reagent for detecting sphingomyelin comprising the protein of the present invention.

A still further aspect of the present invention provides a method for detecting sphingomyelin using the protein of the present invention.

A still further aspect of the present invention provides a kit for detecting sphingomyelin, which comprises the protein, the gene, the vector, the transformant, or the reagent for detecting sphingomyelin according to the present invention.

DETAILED DESCRIPTION OF THE INVENTION

Figure 1:
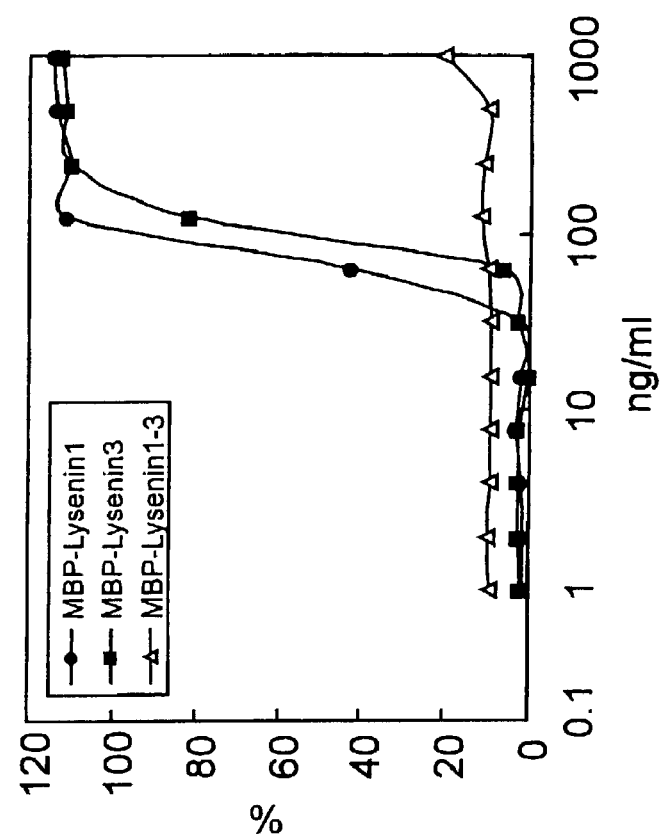
FIG. 1 shows a result of an experiment for the confirmation of reactivity between the protein of Example 1 of the present invention and sphingomyelin by ELISA (on left graph), and a result of hemolysis experiment using the protein of Example 1 of the present (on right graph).
Figure 1:
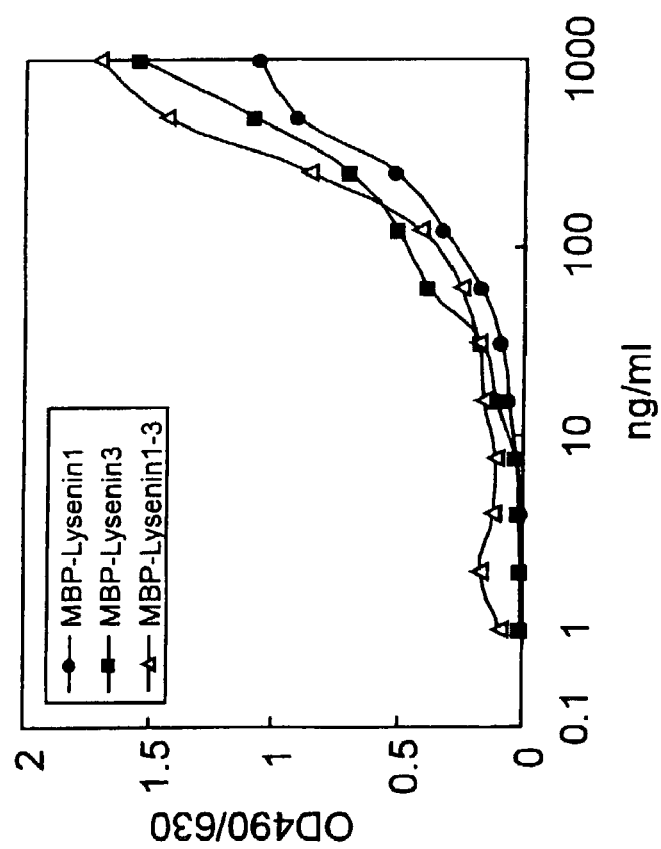

The embodiments of the present invention will now be described in detail.

(A) Proteins of the Present Invention

The first protein of the present invention has either of the following amino acid sequences:

(1) an amino acid sequence having, as the amino acid sequence from the 1st to the 48th amino acid, the amino acid sequence from the 1st to the 48th amino acid in Lysenin 1, and as the amino acid sequence from the 49th to the 298th amino acid, the amino acid sequence from the 51st to the 300th amino acid in Lysenin 3; or
 (2) an amino acid sequence derived from the amino acid sequence according to (1) above by substitution, deletion, and/or addition of one or more amino acids, which specifically recognizes sphingomyelin and has low cytotoxicity.

More specifically, the first protein of the present invention has either of the following an amino acid sequences:
 (1) the amino acid sequence of SEQ ID NO: 3; or
 (2) an amino acid sequence derived from the amino acid sequence of SEQ ID NO: 3 by substitution, deletion, and/or addition of one or more amino acids, which specifically recognizes sphingomyelin and has low cytotoxicity.

The second protein of the present invention is a protein obtained by deleting N terminal and/or C terminal of *Eisenia foetida* toxins Lysenin 1 or 3, which specifically recognizes sphingomyelin. The portion to be deleted in the amino acid sequence of Lysenin 1 or 3 may be N terminal or C terminal, and both of N terminal or C terminal may be detelted. Preferably, N terminal may be deleted. The number of the amino acid residues to be deleted is not particularly limited so long as the obtained protein can specifically recognizes sphingomyelin. Preferably, at least 50 amino acid residues are deleted, and more preferably 70 amino acid residues or more, and still more preferably 100 amino acid residues can be deleted. The upper limit of the number of the amino acid residues to be deleted is preferably 200 or less.

More specifically, the second protein of the present invention has either of the following an amino acid sequences:
 (1) the amino acid sequence of SEQ ID NO: 5; or
 (2) an amino acid sequence derived from the amino acid sequence of SEQ ID NO: 5 by substitution, deletion, and/or addition of one or more amino acids, which specifically recognizes sphingomyelin and has low cytotoxicity.

The range of "one or more" in the phrase "an amino acid sequence derived from the amino acid sequence . . . by substitution, deletion, and/or addition of one or more amino acids" is not particularly limited. For example, it means about 1 to 50, preferably 1 to 20, more preferably 1 to 10, more preferably 1 to 7, still more preferably 1 to 5, and particularly preferably 1 to 3.

The phrase "specifically recognizes sphingomyelin" used herein means that, for example, in ELISA (enzyme-linked immunosorbent assay), a reaction with sphingomyelin is observed while reactivity with phosphatidylcholine is low.

In order for the protein of the present invention to specifically recognize sphingomyelin, among the amino acid residues, tryptophan (Trp) is preferably maintained. That is, in a preferred embodiment of the present invention, the 20th, the 116th, the 187th, the 245th, and the 291st tryptophan residues in the amino acid sequence of SEQ ID NO: 3 in the Sequence Listing are maintained, and the 70th, the 128th, and the 174st tryptophan residues in the amino acid sequence of SEQ ID NO: 5 in the Sequence Listing are maintained.

The term "cytotoxicity" used herein can be confirmed by measuring the hemolysis activity of the red blood cell. For example, the hemolysis activity can be measured by adding test proteins at various concentrations to the sheep red blood cell, performing a reaction at 37° C. for 30 minutes, precipitating the blood cells by centrifugation, and then measuring the amount of hemoglobin released by cell disruption as the absorbancy at 405 nm. One feature of the protein of the present invention is that it has low cytotoxicity which is measured in a manner as described above.

Methods for obtaining and producing the protein of the present invention are not particularly limited. The protein may be either of a chemically synthesized protein or a recombinant protein produced by gene recombination techniques. A recombinant protein is preferred from the viewpoint of the large scale production with a relatively simple procedure.

When obtaining chemically synthesized proteins, for example, the protein of the present invention can be synthesized according to chemical synthesis methods such as Fmoc synthesis (fluorenylmethyloxycarbonyl synthesis) and t-Boc synthesis (t-butyloxycarbonyl synthesis). Various commercially available peptide synthesizers can be used to synthesize the protein of the present invention, for example, those manufactured by Sowa Trading Co., Inc. (manufactured by Advanced Chem Tech, USA), Perkin-Elmer Japan (manufactured by Perkin-Elmer, USA), Pharmacia Biotech (manufactured by Pharmacia Biotech, Sweden), Aloka Co. (manufactured by Protein Technology Instrument, USA), KURABO INDUSTRIES LTD. (manufactured by Synthecell-Vega, USA), Nihon PerSeptive Limited (manufactured by PerSeptive, USA), and Shimadzu Corp.

The protein of the present invention can be produced as a recombinant protein by obtaining DNA having a nucleotide sequence which encodes the protein (for example, a nucleotide sequence of SEQ ID NO: 3 or SEQ ID NO: 4) or a variant or homologue thereof and introducing it into a preferable expression system. Production of an expression vector and a transformant, and production of a recombinant protein using it is hereinafter described.

Regarding the protein comprising an amino acid sequence derived from the amino acid sequence of SEQ ID NO: 3 or SEQ ID NO: 5 by substitution, deletion, and/or addition of one or more amino acids, which specifically recognizes sphingomyelin and has low cytotoxicity, an ordinarily skilled person in the art can appropriately produce such protein based on the information on the nucleotide sequence of SEQ ID NO: 4 that shows an example of a DNA sequence coding for the amino acid sequence of SEQ ID NO: 3, or the information on the nucleotide sequence of SEQ ID NO: 6 that shows an example of a DNA sequence coding for the amino acid sequence of SEQ ID NO: 5.

(B) Genes of the Present Invention

The present invention also relates to a gene which encodes the protein of the present invention.

Specific examples of the gene which encodes the first protein of present invention include genes having either of the following nucleotide sequences:

(1) the nucleotide sequence of SEQ ID NO: 4; or (2) a nucleotide sequence derived from the nucleotide sequence of SEQ ID NO: 4 by substitution, deletion, and/or addition of one or more nucleotides, which specifically recognizes sphingomyelin and codes for a protein having low cytotoxicity.

Specific examples of the gene which encodes the second protein of present invention include genes having either of the following nucleotide sequences:

(1) the nucleotide sequence of SEQ ID NO: 6; or (2) a nucleotide sequence derived from the nucleotide sequence of SEQ ID NO: 6 by substitution, deletion, and/or addition of one or more nucleotides, which specifically recognizes sphingomyelin and codes for a protein having low cytotoxicity.

The range of "one or more" in "a nucleotide sequence derived from the nucleotide sequence of SEQ ID NO: 4 pr 6 by substitution, deletion, and/or addition of one or more nucleotides" is not particularly limited. For example, it means about 1 to 150, preferably 1 to 60, more preferably 1 to 30, more preferably 1 to 20, still more preferably 1 to 10, and particularly preferably 1 to 5.

A method for obtaining the gene of the present invention is not particularly limited. Adequate primers can be prepared in accordance with information on the nucleotide sequence and the amino acid sequence according to SEQ ID NOs: 1 and 13 (the nucleotide sequence and the amino acid sequence of Lysenin 1), SEQ ID NOs: 2 and 14 (the nucleotide sequence and the amino acid sequence of Lysenin 3), SEQ ID NO: 3 (the amino acid sequence of the chimera protein of the present invention comprising Lysenins 1 and 3 prepared in the following example 1), SEQ ID NO: 4 (the nucleotide sequence of the chimera protein of the present invention comprising Lysenins 1 and 3 prepared in the following example 1), SEQ ID NO: 5 (the 118st to 297st amino acid residues of Lysenin 1), and SEQ ID NO: 6 (the nucleotide sequence encoding the 118st to 297st amino acid residues of Lysenin 1) in Sequence Listing provided herein. The gene of the present invention can be prepared by using such primers.

The gene (variant gene) comprising a "nucleotide sequence derived from the nucleotide sequence of SEQ ID NO: 4 or SEQ ID NO: 6 by substitution, deletion, and/or addition of one or more nucleotides, which encodes a protein which specifically recognizes sphingomyelin and has low cytotoxicity" can be prepared by any conventional methods for an ordinarily skilled person in the art, such as chemical synthesis, genetic engineering or mutagenesis.

This type of variant gene can be obtained by, for example, utilizing DNA comprising the nucleotide sequence of SEQ ID NO: 4 or SEQ ID NO: 6, and introducing variation into the DNA. More specifically, DNA having the nucleotide sequence of SEQ ID NO: 4 or SEQ ID NO: 6 can be contacted with an agent for mutagen, or can be subjected to ultraviolet irradiation or a genetic engineering technique. Site-directed mutagenesis which is one genetic engineering technique is useful since specific mutation can be introduced into a specific position. Site-directed mutagenesis can be carried out in accordance with methods described in, for example, Molecular Cloning: A Laboratory Manual, $2^{nd}$ Ed., Cold Spring Harbor Laboratory, Cold Spring Harbor, N.Y., 1989; or Current Protocols in Molecular Biology, Supplement 1–38, John Wiley & Sons (1987–1997).

(C) Vector Having the Gene of the Present Invention

The gene of the present invention can be incorporated into a suitable vector, and can be used as a recombinant vector. A vector may be expression vecor or non-expression vector, and can be selected depending on its use.

As cloning vectors, those capable of autonomous replication in *Escherichia coli* K12 strain are preferred. Any vectors, such as a phage vector or plasmid vector, can be used. Specific examples thereof include ZAP Express, pBluescript II SK(+), Lambda ZAP II (manufactured by Stratagene), λgt10, λgt11, and λTriplEx (manufactured by CloneTech), λExCell (manufactured by Pharmacia), pT7T318U (manufactured by Pharmacia), pcD2, pMW218 (manufactured by Wako Pure Chemical Industries, Ltd.), pUC118 (manufactured by TAKARA SHUZO CO., LTD), and pQE-30 (manufactured by QIAGEN).

A preferred expression vector used herein is one that is capable of autonomous replication in a host cell, or one that is capable of incorporation into a chromosome of a host cell. A vector containing a promoter in a such position that the gene of the present invention can be expressed is used as an expression vector.

When a bacterium is used as the host cell, the expression vector for expressing the gene of the present invention is preferably capable of autonomous replication in the bacterium, and is also preferably a recombinant vector composed of a promoter, a ribosome binding sequence, the above-described DNA, and a transcription termination sequence. A gene controlling the promoter may be contained therein.

Expression vectors for bacteria include, for example, pBTrP2, pBTac1, and pBTac2 (commercially available from Boehringer Mannheim), pKK233-2 (manufactured by Pharmacia), pSE280 (manufactured by Invitrogen), pGEMEX-1 (manufactured by Promega), pQE-8 (manufactured by QIAGEN), pQE-30 (manufactured by QIAGEN), pKYP10 (Japanese Patent Application Laying-Open No. 58-110600), pKYP200 [Agrc. Biol. Chem., 48, 669 (1984)], PLSA1 [Agrc. Biol. Chem., 53, 277 (1989)], pGEL1 [Proc. Natl. Acad. Sci. USA, 82, 4306 (1985)], pBluescrlptII SK+, pBluescriptII SK(−) (manufactured by Stratagene), pTrS30 (FERMBP-5407), pTrS32 (FERM BP-5408), pGEX (manufactured by Pharmacia), pET-3 (manufactured by Novagen), pTerm2 (U.S. Pat No. 4,686,191, U.S. Pat No. 4,939,094, U.S. Pat No. 5,160,735), pSupex, pUB110, pTP5, pC194, pUC18 [Gene, 33, 103 (1985)], pUC19 [Gene, 33, 103 (1985)], pSTV28 (manufactured by TAKARA SHUZO CO., LTD), pSTV29 (manufactured by TAKARA SHUZO CO., LTD), pUC118 (manufactured by TAKARA SHUZO CO., LTD), and pQE-30 (manufactured by QIAGEN). Promoters for bacteria include, for example, a promoter derived from *Escherichia coli* or phage such as a trp promoter (P trp), a lac promoter (P lac), a $P_L$ promoter, a $P_R$ promoter, or a $P_{SE}$ promoter; a SP01 promoter; a SP02 promoter, and a penP promoter.

Examples of expression vectors for yeast include YEp13 (ATCC37115), YEp24 (ATCC37051), Ycp5O (ATCC37419), pHS19, and pHS15. Promoters for yeast include, for example, a PHO5 promoter, a PGK promoter, a GAP promoter, an ADH promoter, a gal1 promoter, a gal10 promoter, a heat-shock protein promoter, an MFα1 promoter, and a CUP1 promoter.

Examples of expression vectors for animal cells include pcDNAI, pcDM8 (commercially available from Funakoshi), pAGE107 [Japanese Patent Application Laying-Open No. 3-22979; Cytotechnology, 3, 133, (1990)], pAS3-3 (Japanese Patent Application Laying-Open No. 2-227075), pCDM8 [Nature, 329, 840, (1987)], pcDNAI/AmP (manufactured by Invitrogen), pREP4 (manufactured by Invitrogen), pAGE103 [J. Blochem., 101, 1307 (1987)], and pAGE210. Promoters for animal cells include, for example, a promoter of cytomegalovirus (human CMV) IE (immediate early) gene, an SV-40 early promoter, a retrovirus promoter, a metallothionein promoter, a heat-shock promoter, and an SRα promoter.

Examples of expression vectors for plant cells include pIG121-Hm [Plant Cell Report, 15, 809–814(1995)] and pBI121 [EMBO J. 6, 3901–3907(1987)]. Promoters for plant cells include, for example, a cauliflower mosaic virus 35S promoter [Mol. Gen. Genet (1990) 220, 389–392] and a ribulose bisphosphate carboxylase small subunit promoter.

(D) Transformant Having the Gene of the Present Invention

The transformant having the gene coding for the protein of the present invention can be produced by introducing the recombinant vector (preferably an expression vector) into a host.

Examples of bacteria host cells include microorganisms belonging to the genus *Escherichia*, the genus *Corynebacterium*, the genus *Brevibacterium*, the genus *Bacillus*, the genus *Microbacterium*, the genus *Serratia*, the genus *Pseudomonas*, the genus *Agrobacterium*, the genus *Alicyclobacillus*, the genus *Anabaena*, the genus *Anacystis*, the genus *Arthrobacter*, the genus *Azobacter*, the genus *Chromatium*, the genus *Erwinia*, the genus *Methylobacterium*, the genus *Phormidium*, the genus *Rhodobacter*, the genus *Rhodopseudomonas*, the genus *Rhodospirillum*, the genus *Scenedesmun*, the genus *Streptomyces*, the genus *Synnecoccus*, and the genus *Zymomonas*. Methods for introducing a recombinant vector into a bacteria host cell include, for example, the calcium ion method and the protoplast method.

Examples of a yeast host include *Saccharomyces cerevisae*, *Schizosaccharomyces pombe*, *Kluyveromyces lactis*, *Trichosporon pullulans*, and *Schwanniomyces alluvius*. Methods for introducing a recombinant vector into a yeast host include, for example, an electroporation method, a spheroplast method, and a lithium acetate method.

Examples of animal host cells include Namalwa cell, COS1 cell, COS7 cell, and CHO cell. Methods for introducing a recombinant vector into animal cells include, for example, an electroporation method, a calcium phosphate method, and a ripofection method.

When insect cells are used as the host, a recombinant gene introducing vector and a baculovirus are co-introduced into the insect cell, a recombinant virus is obtained in a supernatant of the insect cell culture, and the insect cell is infected with the recombinant virus. Thus, a protein can be expressed (for example, as described in Baculovirus Expression Vectors, A Laboratory Manual; and Current Protocols in Molecular Biology, Bio/Technology, 6, 47 (1988)).

Baculoviruses used herein include, for example, *Autographa californica* nuclear polyhedrosis virus, which is a virus infected with an insect of species *Mamestra*.

Examples of insect cells used herein include Sf9 and Sf21, which are ovarian cells of *Spodoptera frugiperda* [Baculovirus Expression Vectors, A Laboratory Manual, W. H. Freeman and Company (New York, 1992)], and HiFive, which is an ovarian cell of *Trichoplusia ni* (manufactured by Invitrogen).

Methods for co-introducing the recombinant gene introducing vector and the baculovirus into the insect cell for the preparation of a recombinant virus include, for example, a calcium phosphate method and a ripofection method.

(E) Production of a Recombinant Protein Using the Transformant of the Present Invention According to the present invention, a recombinant protein can be isolated by culturing a transformant having the gene of the present invention that is produced as above, producing and accumulating the protein of the present invention in the cultured product, and collecting the protein of the present invention from the cultured product.

When the transformant of the present invention is a prokaryotic organism such as *Escherichia coli* or an eukaryotic organism such as a yeast, the medium for culturing these microorganisms may be either a natural or synthetic culture medium, as long as the medium comprises a carbon source, a nitrogen source, an inorganic base and the like, which the microorganism can assimilate, and the culturing of the transformant can be efficiently carried out. The culturing is preferably carried out under an aerobic condition, the culture temperature is generally from 15 to 40° C., and the culture time is generally from 16 hours to 7 days. The pH value of the culture solution can be adjusted using an inorganic or organic acid, an alkaline solution, urea, calcium carbonate, ammonia and the like. If necessary, antibiotics such as Ampicillin or tetracycline may be added to the medium while culturing.

As a medium for culturing the transformant prepared using animal cells as the host cell, commonly used RPM11640 medium, Eagle's MEM medium or DMEM medium, or a medium prepared by adding fetal bovine serum or the like to these mediums, are used. The culturing is generally carried out, for example, at a pH value of 6 to 8 at 30 to 40° C. in the presence of 5% $CO_2$ for 1 to 7 days. While culturing, antibiotics such as kanamycin and penicillin may be added to the medium if necessary.

As a medium for culturing the transformant prepared using plant cells as the host cell, commonly used media such as MS medium and R2P medium are used depending on the type of the plant. The culturing is generally carried out at a pH value of 6 to 8 at 15 to 35° C. for 1 to 21 days. While culturing, antibiotics such as kanamycin and hygromycin may be added to the medium if necessary.

In order to isolate and purify the protein of the present invention from a cultured product of the transformant, a conventional isolation-purification method for the protein may be employed.

For example, when the protein of the present invention is expressed in a dissolved state in the cell, after the completion of culturing, cells are collected by centrifugation, suspended in an aqueous buffer solution, and fragmented using, for example, an ultrasonic crusher, French press, Menton-Gaulin homogenizer, or DYNO-Mill to obtain a cell-free extract. The cell-free extract is centrifuged to obtain a supernatant. The resultant supernatant is subjected to conventional techniques for isolating and purifying proteins, that is, techniques such as solvent extraction, salting-out using ammonium sulfate and the like, desalination, precipitation using organic solvents, anion exchange chromatography using resins such as diethyl amino ethyl (DEAE) sepharose, cation exchange chromatography using resins such as S-Sepharose FF (manufactured by Pharmacia), hydrophobic chromatography using resins such as butyl sepharose and phenyl sepharose, gel filtration using a molecular sieve, affinity chromatography, chromatofocusing, and electrophoresis such as isoelectric focusing. These methods may be carried out alone or in combination of two or more to obtain purified preparations.

(F) Reagent for Detecting Sphingomyelin

The present invention also relates to a reagent for detecting sphingomyelin which comprising the protein of the present invention. The protein of the present invention can specifically recognize sphingomyelin, and thus is useful as a reagent for detecting sphingomyelin. When the protein of the present invention is used as a reagent for detecting sphingomyelin, it may be used alone or may be used as a labeled protein that is labeled with substances for detection. The types of labeling substances for detection are not particularly limited and include, for example, affinity substances such as maltose-binding protein, biotin, avidin, and streptavidin; enzymes such as horseradish peroxidase and alkaline phosphatase; fluorescent substances such as Cy5 and Cy3 (Amersham), fluorescein, tetramethylrhodamine, Texas Red, and acridine orange; chemiluminescent substances such as luminol and acridinium-I; and radioactive substances.

(G) Method for Detecting Sphingomyelin Using the Protein of the Present Invention The protein of the present invention specifically recognizes sphingomyelin and has low cytotoxicity. Therefore, sphingomyelin can be detected by using the protein of the present invention as a probe.

A method for detecting sphingomyelin is not particularly limited, and may be an in vitro method such as ELISA or an in vivo method such as cell staining.

In order to perform ELISA, an ELISA plate is coated with a sphingomyelin-containing sample and blocked with bovine serum albumin or the like. Thereafter, the protein of the present invention is added to the plate, and incubation is carried out. After washing the plate, suitable reagents for detecting the protein of the present invention are successively added thereto and reacted, thereby detecting sphingomyelin in the sample. For example, when the protein of the present invention having an MBP (maltose-binding protein) sequence is used as a detecting probe, after the reaction with the sample, the sample is incubated with an anti-MBP rabbit serum, and is washed. Subsequently, incubation is carried out using a biotin-labeled anti-rabbit antibody and horseradish peroxidase (HRP)-labeled streptavidin, color is developed with o-phenylendiamine, and the absorbancy at 492 nm is measured. Thus, sphingomyelin in the sample can be detected.

In order to perform cell staining, for example, after the cell is immobilized on a cover slip, a plasma membrane is holed through a digitonin treatment, followed by reaction with the protein of the present invention. After the reaction, suitable reagents for detecting the protein of the present invention are successively added thereto and reacted, thereby detecting sphingomyelin in the cell. For example, when the protein of the present invention having an MBP (maltose-binding protein) sequence is used as a detecting probe, after the reaction with the cell, incubation is carried out using diluted anti-MBP rabbit serum (NEB) and a fluorescent-labeled anti-rabbit antibody, followed by inclusion. Then, cells are observed under a confocal microscope, thereby detecting sphingomyelin in the cell.

(H) Kit for Detecting Sphingomyelin

The protein, the gene, the vector, the transformant, and the reagent for detecting sphingomyelin according to the present invention as described herein, can be provided in the form of a kit for detecting sphingomyelin. The kit for detecting sphingomyelin can comprise the protein, the gene, the vector, the transformant, or the reagent for detecting sphingomyelin, as well as other necessary reagents if desired. Such other reagents include, for example, a buffer solution required in the reaction, a blocking solution, washing solution, and other reagents required in the detection of labels. A ordinarily skilled person in the art can appropriately select such reagents, and can construct a kit.

The present invention will now be described in more detail with reference to the following examples although it is not limited to these examples only.

EXAMPLES

Example 1

(A) Cloning of cDNA of Earthworm Toxin Lysenin

Cloning of cDNA of earthworm toxin Lysenin has been already reported (Sekizawa, Y., Kubo, T., Kobayashi, H., Nakajima, T., and Natori, S. (1997), Molecular cloning of cDNA for lysenin, a novel protein in the earthworm *Eisenia foetida* that causes contraction of rat vascular smooth muscle. Gene 191, 97–102). Also, the nucleotide sequences of Lysenin 1 and Lysenin 3 are registered in a database (Lysenin 1: GenBank85846; and Lysenin 3: GenBank85848). The nucleotide sequence and the amino acid sequence of Lysenin 1 are shown in SEQ ID NO: 1 in Sequence Listing, and the nucleotide sequence and the amino acid sequence of Lysenin 3 are shown in SEQ ID NO: 2 in Sequence Listing.

(B) Production of MBP-Lysenin 1–3

(1) Production of pMBP-Lysenin 1, pMBP-Lysenin 3

In the amplification by PCR, the following primers in which the 5'-terminus is BamHI site and the 3'-terminus is HindIII site were prepared for both Lysenins 1 and 3.

Lysenin 1 forward: ttcggatccatgtcggctaaagcagca (SEQ ID NO: 7)

Lysenin 1 reverse: aagcttccgctttagttgcacctcatc (SEQ ID NO: 8)

Lysenin 3 forward: ttcggatccatgtcgtctagagcagga (SEQ ID NO: 9)

Lysenin 3 reverse: aagcttaaaacatgcggaagcaaatgt (SEQ ID NO: 10)

The full lengths of Lysenin 1 and Lysenin 3 were amplified by PCR using cDNA obtained in (A) above as a template, and then were cloned into PCR-TOPOII vector (Invitrogen). Thereafter, the complete nucleotide sequences were confirmed. The above plasmids were treated with BamHI and HindIII, a fragment containing Lysenin was collected and was ligated to pMAL-C2X (New England Biolab) which was also treated with BamHI and HindIII, to obtain plasmids having an MBP (maltose-binding protein) sequence at the 5' terminus, i.e., pMBP-Lysenin 1 and pMBP-Lysenin 3.

(2) Production of pMBP-Lysenin 1–3

EcoRI site is present at 141 bp in pMBP-Lysenin 1 and at 147 bp in pMBP-Lysenin 3. Also, pMAL-C2X has EcoRI site at a position of 2695 bp (BamHI is located at 2701 bp and HindIII at 2727 bp). pMBP-Lysenin 1 and pMBP-Lysenin 3 were respectively treated with EcoRI, and the 5'-terminus of Lysenin 3 was replaced with Lysenin 1. EcoRI corresponds to valine at the 47th position, asparagin at the 48th position, and serine at the 49th position in Lysenin 1, and EcoRI corresponds to leucine at the 49th position, asparagin at the 50th position, and serine at the 51st position in Lysenin 3. Therefore, Lysenin 1–3 is a chimera in which the region from methionine at the 1st position to asparagin at the 48th position is obtained from Lysenin 1, and the region from serine at the 51st position to proline at the 300th position is obtained from Lysenin 3.

(C) Expression of Protein

The above plasmid was transformed into *Escherichia coli* JM109 and, in accordance with a conventional method, protein expression was induced using IPTG, bacteria were collected, and solubilization by sonication was carried out. Further, after affinity purification was carried out using amylose resin (NEB), expression was confirmed by silver staining and Western blotting using an anti-MBP antibody.

(D) Confirmation of Specific Reaction Between the Protein of the Present Invention and Sphingomyelin by ELISA (Enzyme-linked Immunosorbent Assay)

A 96-well ELISA plate (Immulon 1, Dynatech Laboratories) was coated with 10 μM of sphingomyelin (SM) (phosphatidylcholine as control). After blocking with 3% bovine serum albumin (BSA), MBP-Lysenin 1, MBP-Lysenin 3, and MBP-Lysenin 1–3 were respectively diluted into a suitable amount, and were added. The plate was incubated at room temperature for 2 hours. After the plate was washed three times, an anti-MBP rabbit serum (NEB) which was diluted to 1:1000, was added, and incubation was carried out for 2 hours and the plate was then washed. Further, incubation was carried out using a biotin-labeled anti-rabbit antibody and horseradish peroxidase (HRP)-labeled streptavidin, color was developed with o-phenylendiamine, and the absorbancy at 492 nm (630 nm as control) was measured.

Figure 3:
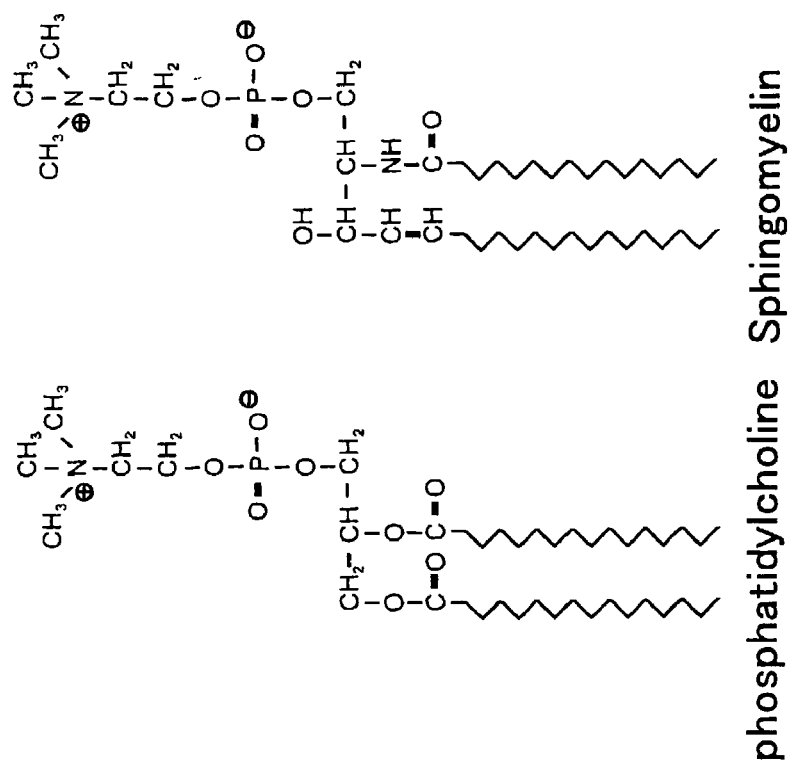
FIG. 3 shows (1) a result of an experiment for the confirmation of specific reactivity between the protein of Example 1 of the present invention and sphingomyelin of ELISA, and (2) the chemical structures of phosphatidylcholine and sphinpomyelin.
Figure 3:
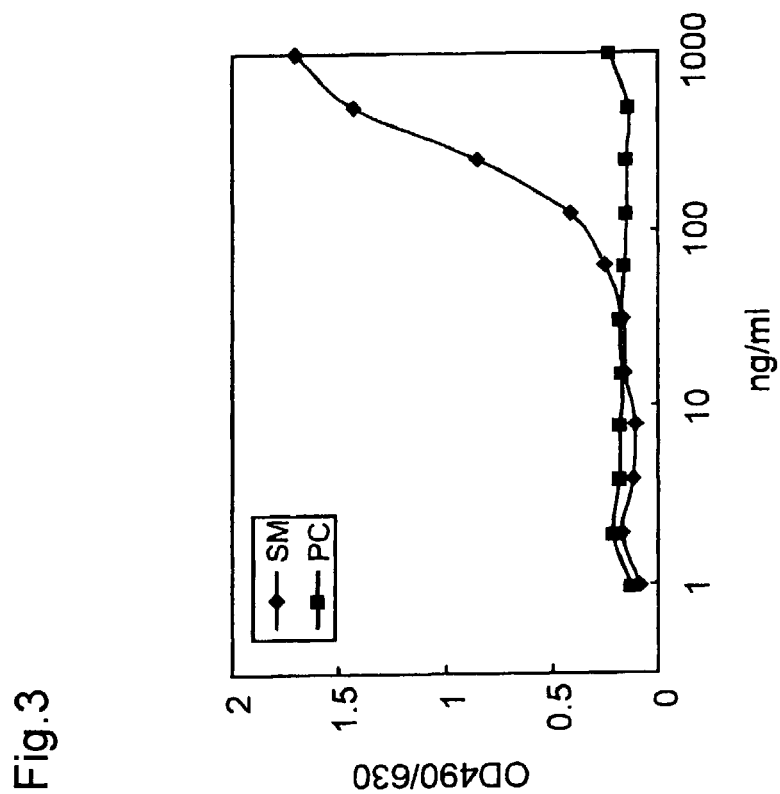

The results are shown in FIG. 1, left graph, and in FIG. 3. These results indicate that MBP-Lysenin 1–3 specifically binds to sphingomyelin, as is the case with MBP-Lysenin 1 and MBP-Lysenin 3.

(E) Hemolysis

MBP-Lysenin 1, MBP-Lysenin 3 and MBP-Lysenin 1–3 at various concentrations were added to $3 \times 10^7$ cells/mL of the sheep red blood cell, followed by a reaction at 37° C. for 30 minutes. The blood cells were precipitated by centrifugation, and the amount of hemoglobin released by cell disruption was measured as the absorbancy at 405 nm. The value obtained when all the cells were disrupted was taken as 100%, and values at each point were calculated.

The results are shown in FIG. 1, right graph. These results indicate that MBP-Lysenin 1 and MBP-Lysenin 3 exhibit hemolysis activity at a certain concentration or higher, while MBP-Lysenin 1–3 does not exhibit hemolysis activity even at a high concentration.

(F) Cell Staining Using Niemann-Pick Type A Fibroblast

A fibroblast obtained from a patient suffering from Niemann-Pick disease type A was cultured on a glass cover slip for several days. After fixing with paraformaldehyde, a plasma membrane was holed by a digitonin treatment, followed by reaction with MBP-Lysenin 1, MBP-Lysenin-3, or MBP-Lysenin 1–3. Incubation was carried out using diluted anti-MBP rabbit serum (NEB) and a fluorescent-labeled anti-rabbit antibody, followed by inclusion, and observation under a confocal microscope.

Figure 2:
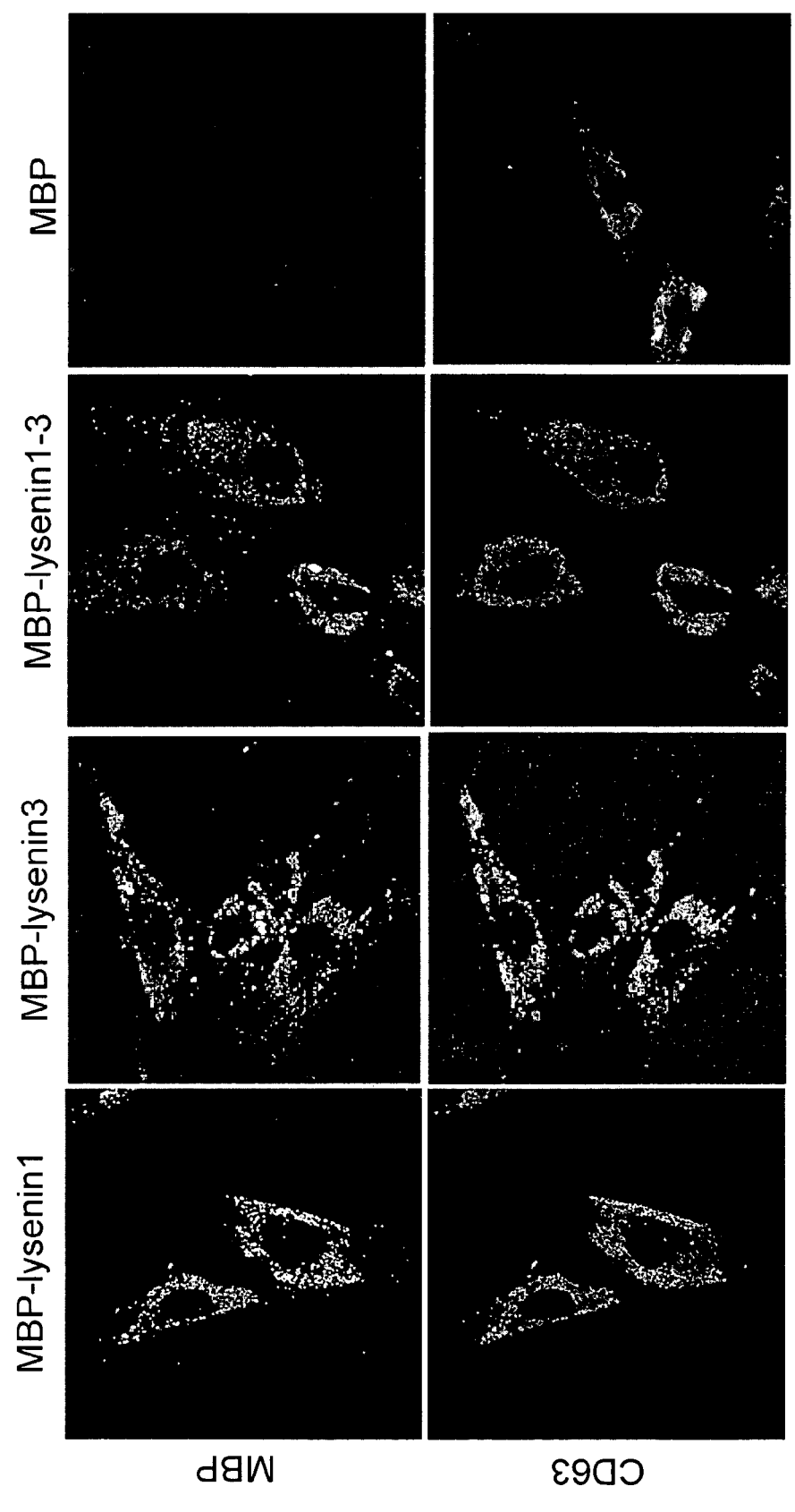
FIG. 2 shows a result of cell staining using the protein of Example 1 of the present invention and Niemann-Pick type A fibroblast.

The results are shown in FIG. 2. The results shown in FIG. 2 indicate that sphingomyelin of the fibroblast can be detected even in vivo by using MBP-Lysenin 1–3 of the present invention Example 2

(A) Cloning of CDNA of Earthworm Toxin Lysenin

Cloning of cDNA of earthworm toxin Lysenin has been already reported (Sekizawa, Y., Kubo, T., Kobayashi, H., Nakajima, T., and Natori, S. (1997), Molecular cloning of cDNA for lysenin, a novel protein in the earthworm *Eisenia foetida* that causes contraction of rat vascular smooth muscle. Gene 191, 97–102). Also, the nucleotide sequence of Lysenin 1 is registered in a database (GenBank85846). The nucleotide sequence and the amino acid sequence of Lysenin 1 are shown in SEQ ID NO: 1 in Sequence Listing.

(B) Method for Producing MBP-Lysenin 118–297

In amplification by PCR, the following primers capable of amplifying a fragment which is equivalent to amino acids 118–297 in Lysenin 1 (containing nucleotides 351–894 in the nucleotide sequence) and has BamHI site at the 5'-terminus and HindIII site at the 3'-terminus, were prepared.

Lysenin 118 forward: ttcggatccctgaatgxtgacgttggtgga (SEQ ID NO: 11)

Lysenin 1 reverse: aagcttccgctttagttgcacctcatc (SEQ ID NO: 12)

The amino acids 118–297 in Lysenin 1 were amplified by PCR using the above primers using cDNA of Lysenin 1 obtained in (A) above as a template, and then cloned into PCR-TOPOII vector (Invitrogen). Thereafter, a complete nucleotide sequence was confirmed. The above plasmid was treated with BamHI and HindIII, a fragment containing Lysenin was collected and was ligated to pMAL-C2X (New England Biolab) which was also treated with BamHI and HindIII, to obtain a plasmid having an MBP (maltose-binding protein) sequence at its 5' terminus, i.e., pMBP-Lysenin 118–297.

(C) Expression of Protein

The plasmid obtained in above (B) was transformed into *Escherichia coli* JM109 and, in accordance with a conventional method, protein expression was induced using IPTG, bacteria were collected, and solubilization by sonication was carried out. Further, after affinity purification was carried out using amylose resin (NEB), expression was confirmed by silver staining and Western blotting using an anti-MBP antibody.

(D) Confirmation of Specific Reactivity Between the Protein of the Present Invention and Sphingomyelin by ELISA (Enzyme-linked Immunosorbent Assay)

ELISA (enzyme-linked immunosorbent assay) was performed as follows.

A 96-well ELISA plate (Immulon 1, Dynatech Laboratories) was coated with 10 μM of sphingomyelin (phosphatidylcholine as control). After blocking with 3% bovine serum albumin (BSA), MBP-Lysenin 1, MBP, and MBP-Lysenin 118–297 were respectively diluted into a suitable amount, and were added. The plate was incubated at room temperature for 2 hours. After the plate was washed three times, an anti-MBP rabbit serum (NEB) which was diluted to 1:1000, was added, and incubation was carried out for 2 hours and the plate was then washed. Further, incubation was carried out using a biotin-labeled anti-rabbit antibody and horse-radish peroxidase (HRP)-labeled streptavidin, color was developed with o-phenylendiamine, and the absorbancy at 492 nm (630 nm as control) was measured.

Figure 4:
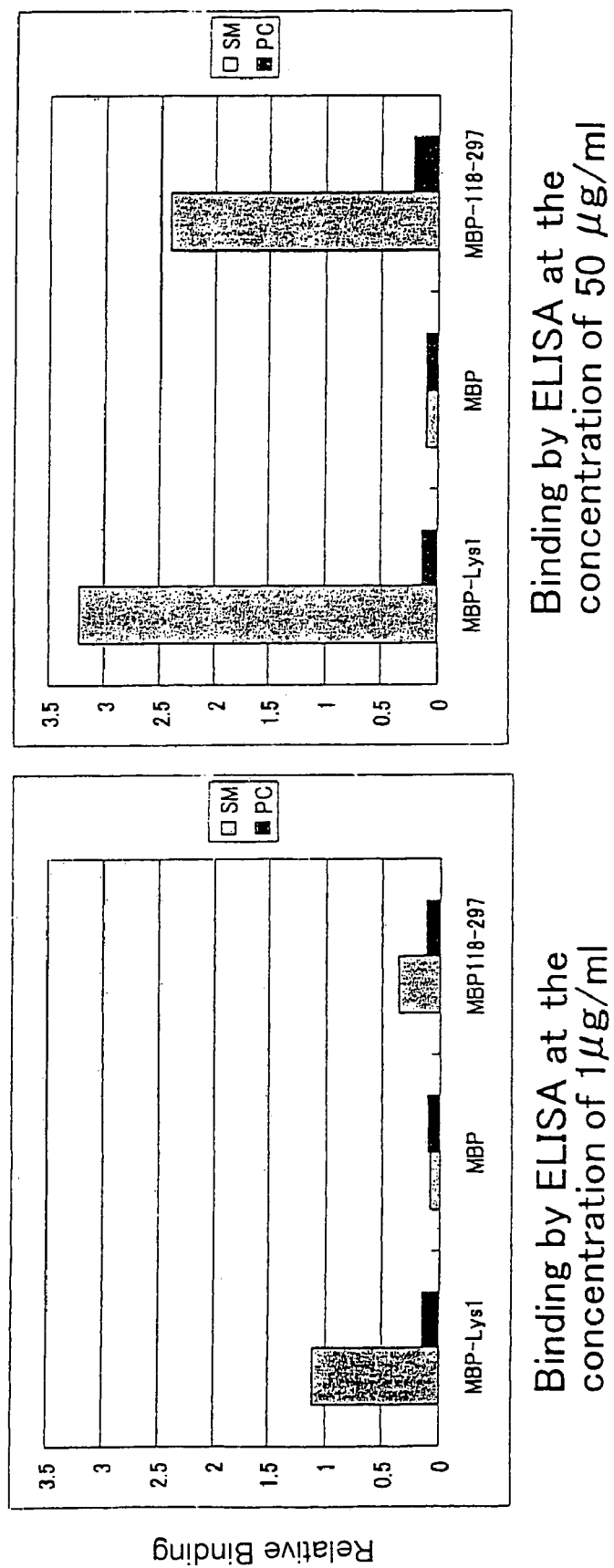
FIG. 4 shows a result of an experiment for the confirmation of reactivity between the protein of Example 2 of the present invention and sphingomyelin by ELISA.

The results are shown in FIG. 4. The results of FIG. 4 indicate that MBP-Lysenin 118–297 specifically binds to sphingomyelin (SM), as is the case with MBP-Lysenin 1.

(E) Hemolysis

MBP-Lysenin 1 and MBP-Lysenin 118–297 at various concentrations were added to 3×10$^7$ cells/mL of the sheep red blood cell, followed by a reaction at 37° C. for 30 minutes. The blood cells were precipitated by centrifugation, and the amount of hemoglobin released by cell disruption was measured as the absorbancy at 405 nm. The value obtained when all the cells were disrupted was taken as 100%, and values at each point were calculated.

Figure 5:
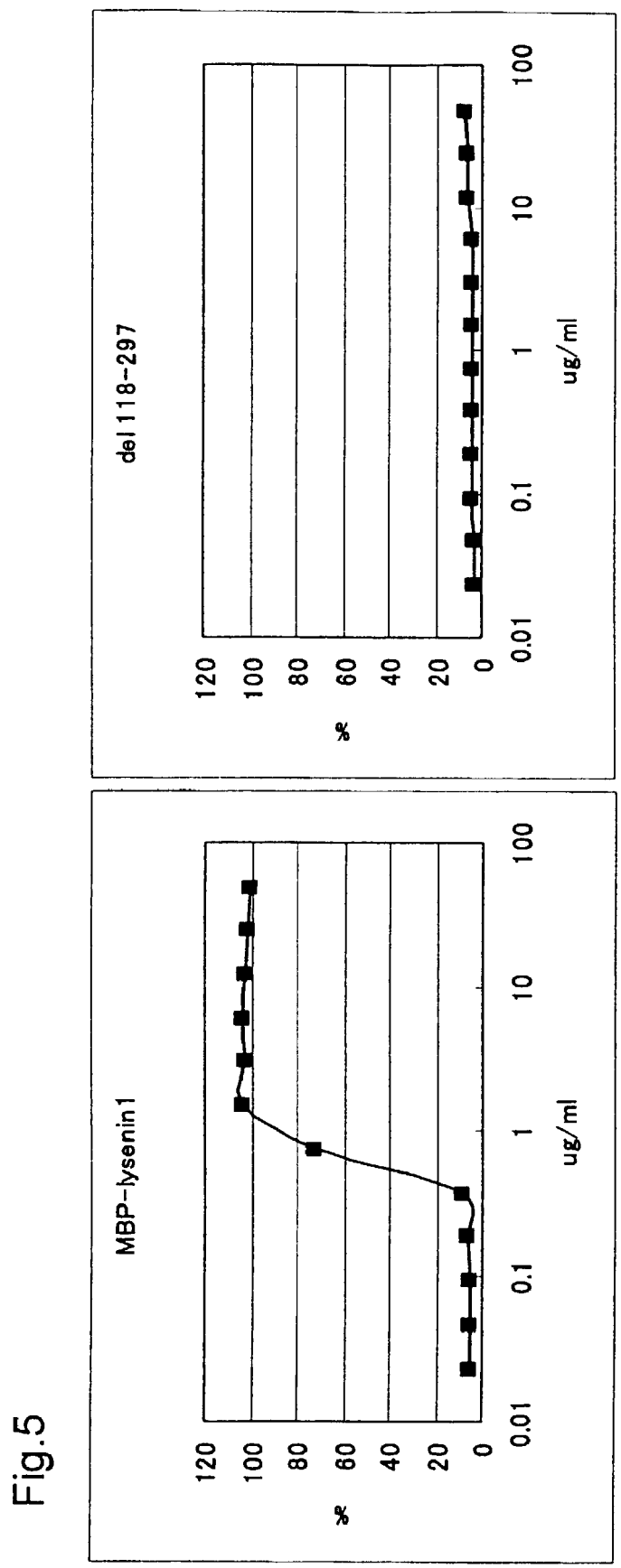
FIG. 5 shows a result of hemolysis experiment using the protein of Example 2 of the present.

The results are shown in FIG. 5. The results of FIG. 5 indicate that that MBP-Lysenin 1 exhibits hemolysis activity at a certain concentration or higher, while MBP-Lysenin 118–297 (indicated as "del 118–297" in FIG. 5) does not exhibit hemolysis activity even at a high concentration.

(F) Cell Staining Using Niemann-Pick Type A Fibroblast

A fibroblast obtained from a patient suffering from Niemann-Pick disease type A was cultured on a glass cover slip for several days. After fixing with paraformaldehyde, a plasma membrane was holed by a digitonin treatment, followed by reaction with MBP-Lysenin 118–297, MBP-Lysenin 1, or MBP. Incubation was carried out using diluted anti-MBP rabbit serum (NEB) and a fluorescent-labeled anti-rabbit antibody, followed by inclusion, and observation under a confocal microscope. At the same time, incubation was carried out using a monoclonal antibody (CALTAG) obtained from a mouse against protein CD 63 existing in the late endosome and a fluorescent-labeled anti-mouse antibody, thereby the late endosome was visualized.

Figure 6:
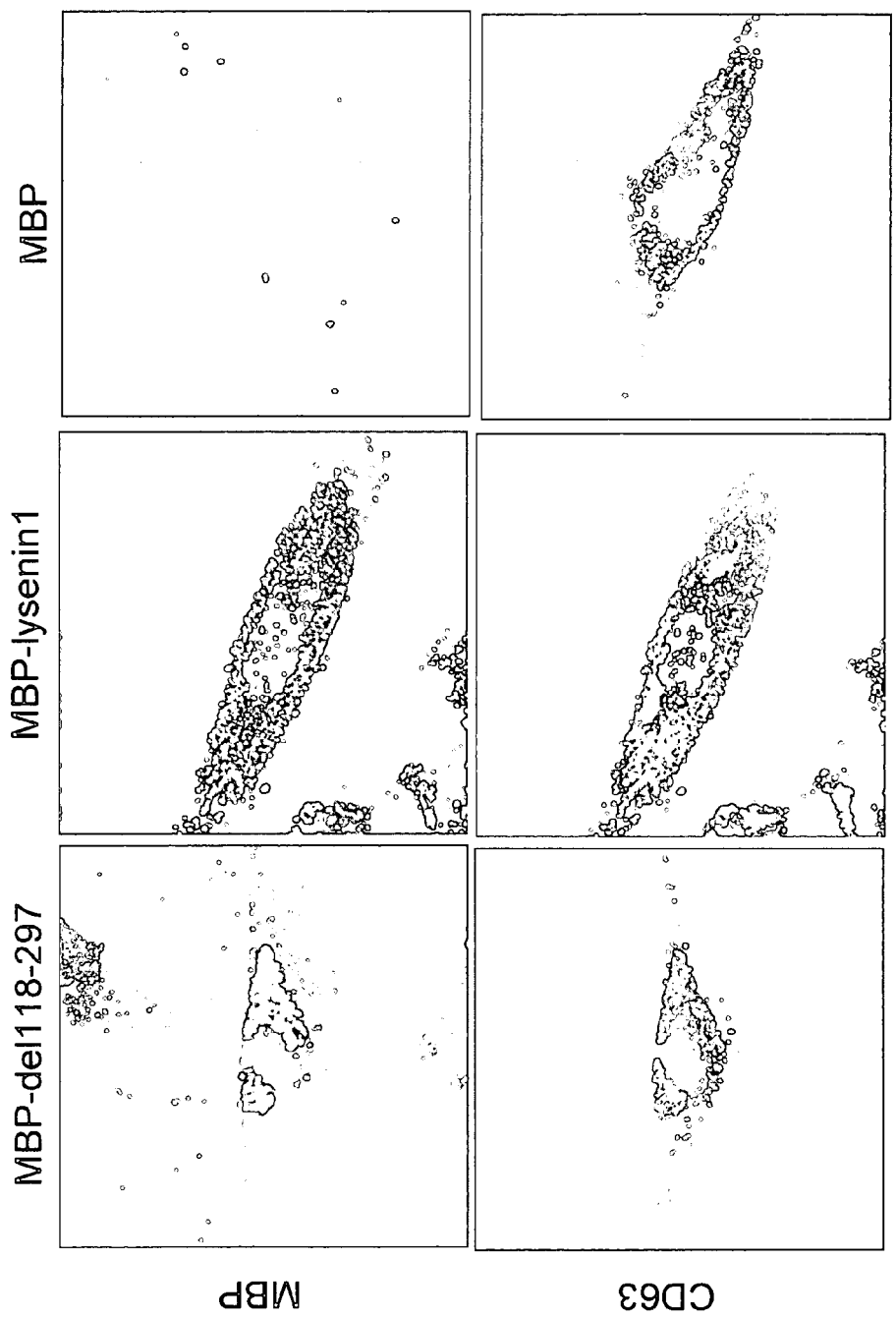
FIG. 6 shows a result of cell staining using the protein of Example 2 of the present invention and Niemann-Pick type A fibroblast.
Figure 7:
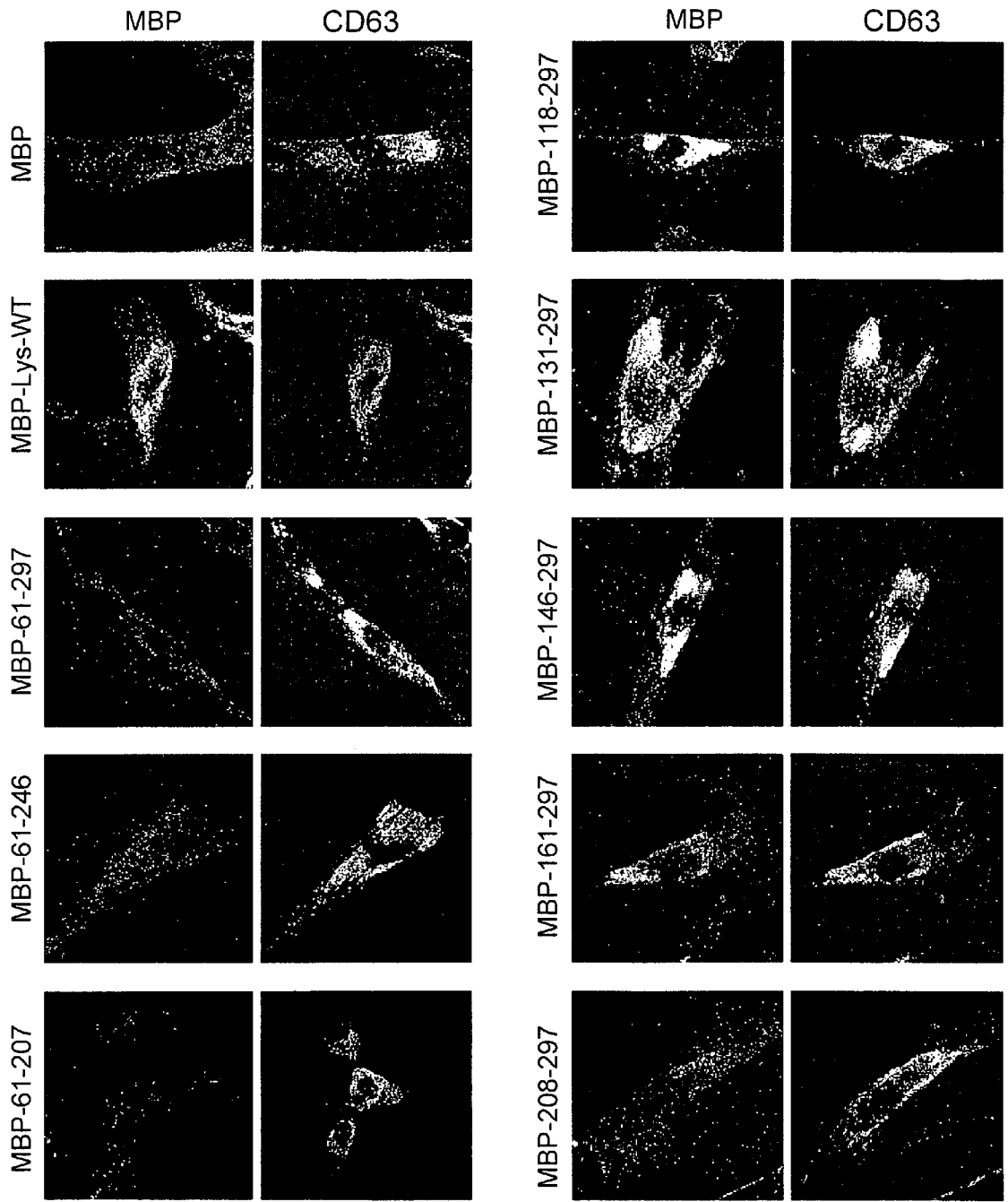
FIG. 7 shows a result of cell staining using the protein of Example 2 of the present invention and Niemann-Pick type A fibroblast.

The results are shown in FIG. 6. The results shown in FIG. 2 indicate that sphingomyelin of the fibroblast can be detected even in vivo by using MBP-Lysenin 118–297 of the present invention A Niemann-Pick type A fibroblast was stained in the same manner as described above. The obtained results are shown in FIG. 7. The results indicate that MBP-61–297, MBP-131–297, MBP-146–297, and MBP-161–297 can be detected in vivo, and suggest that MBP-61–246, MBP-61–207, and MBP-208–297 do not recognize sphingomyelin.

INDUSTRIAL APPLICABILITY

According to the present invention, there can be provided a protein that is usable as a sphingomyelin detecting probe which specifically recognizes sphingomyelin and has low cytotoxicity.

What is claimed is:

1. A protein having either of the following amino acid sequences:
   (1) the amino acid sequence of SEQ ID NO: 3; or
   (2) an isolated amino acid sequence derived from the amino acid sequence of SEQ ID NO: 3 by substitution, deletion, and/or addition of 1 to 10 amino acids and wherein the $20^{th}$, $116^{th}$, $187^{th}$, $245^{th}$, and $291^{st}$ tryptophan residues of the amino acid sequence derived from SEQ ID NO: 3 are not substituted or deleted, which specifically recognizes sphingomyelin and has cytotoxicity lower than that of Lysenin 1 or Lysenin 3 as measured by hemolysis.

2. A gene which encodes the protein of claim 1.

3. A gene having either of the following nucleotide sequences:
   (1) the nucleotide sequence of SEQ ID NO: 4; or
   (2) an isolated nucleotide sequence derived from the nucleotide sequence of SEQ ID NO: 4 by substitution, deletion, and/or addition of 1 to 10 nucleotides which encodes a protein which specifically recognizes sphingomyelin and has cytotoxicity lower than that of Lysenin 1 or Lysenin 3 as measured by hemolysis.

4. A vector having the gene of claim 2.

5. A transformation having the vector of claim 4.

6. A reagent composition for detecting sphingomyelin comprising the protein of claim 1.

7. A method for detecting sphingomyelin comprising:
   (1) adding the protein of claim 1 as a probe to a sample;
   (2) adding at least one reagent; and
   (3) detecting sphingomyelin in the sample.

8. A kit for detecting sphingomyelin, which comprises:
   (a) a protein having either of the following amino acid sequences:
   (1) an amino acid sequence having, as the amino acid sequence from the 1st to the 48th amino acid, the amino acid sequence from the 1st to the 48th amino acid in Lysenin 1, and, as the amino acid sequence from the 49th to the 298th amino acid, the amino acid sequence from the 51st to the 300th amino acid in Lysenin 3; or
   (2) an amino acid sequence derived from the amino acid sequence according to (1) above by substitution, deletion, and/or addition of 1 to 10 amino acids which specifically recognizes sphingomyelin, and has cytotoxicity lower than that of Lysenin 1 or Lysenin 3 as measured by hemolysis, or
   (b) a protein having either of the following amino acid sequences:
   (1) amino acid sequence of SEQ ID NO: 3; or
   (2) an amino acid sequence derived from the amino acid sequence of SEQ ID NO: 3 by substitution, deletion, and/or addition of 1 to 10 amino acids and wherein the $20^{th}$, $116^{th}$, $187^{th}$, $245^{th}$, and $291^{st}$ tryptophan residues of the amino acid sequence derived from SEQ ID NO: 3 are not substituted or deleted, which specifically recognizes sphingomyelin, and has cytotoxicity lower than that of Lysenin 1 or Lysenin 3 as measured by hemolysis, or
   a gene which encodes the protein of (b) above, or a (d) gene having either of the following nucleotide sequences:
   (1) the nucleotide sequence of SEQ ID NO: 4; or
   (2) a nucleotide sequence derived from the nucleotide sequence of SEQ ID NO: 4 by substitution, deletion, and/or addition of 1 to 10 nucleotides, which encodes a protein which specifically recognizes sphingomyelin, and has cytotoxicity lower than that of Lysenin 1 or Lysenin 3 as measured by hemolysis, or
   a vector of the gene of (c), or
   a transformant of the vector of the gene of (c), or
   the reagent for detecting sphingomyelin comprising the protein (a).

* * * * *

UNITED STATES PATENT AND TRADEMARK OFFICE
CERTIFICATE OF CORRECTION

PATENT NO. : 6,995,236 B2
APPLICATION NO. : 10/138634
DATED : February 7, 2006
INVENTOR(S) : T. Kobayashi et al.

It is certified that error appears in the above-identified patent and that said Letters Patent is hereby corrected as shown below:

On the cover of the printed patent, at item (56), References Cited, the following Other Publication was omitted and should be included:
--H Kobayashi, et al Lethal and non-lethal responses of spermatozoa from a wide variety of vertebrates and invertebrates to lysenin, a protein from the coelomic fluid of the earthworm Eisenia foetida. J. Exp. Zool. (2000) 286, 538-549.--

At column 23, line 25 (claim 5, line 1) of the printed patent, "transformation" should be --transformant--.

Signed and Sealed this

Seventeenth Day of October, 2006

JON W. DUDAS
*Director of the United States Patent and Trademark Office*

SEQUENCE LISTING

<160> NUMBER OF SEQ ID NOS: 12

<210> SEQ ID NO 1
<211> LENGTH: 894
<212> TYPE: DNA
<213> ORGANISM: Eisenia fetida

<400> SEQUENCE: 1

```
atgtcggcta aagcagcaga gggatatgaa cagatagaag tagatgtggt ggcagtatgg      60
aaagaaggct atgtatacga aaatcgcgga agcaccagtg tggatcagaa gatcacaata     120
acaaaaggca tgaaaaatgt gaattcagaa acaaggacag tgactgctac gcatagtatt     180
ggttctacta ttagcactgg agatgcattc gaaattggaa gcgtggaggt tagctacagc     240
cattcacatg aagaatccca agttagcatg acggaaactg aagtttatga atcaaaggtg     300
atcgaacaca ctataacgat tccacctact tcaaaattca caagatggca actgaatgct     360
```

```
gacgttggtg gagcggatat tgaatacatg tatttgattg atgaagtcac acccatagga      420
gggactcaga gtattccaca ggtcatcaca agtcgggcta aaattatagt tggccgacag      480
ataatccttg gaaaaacaga aattcgaatt aagcatgcag aaaggaagga gtacatgaca      540
gtcgtttcaa gaaaaagttg gccagctgca actcttggac atagcaaact tttcaagttt      600
gtgctctatg aagattgggg gggatttcga attaaaacgc tgaacaccat gtattcgggc      660
tatgagtatg cctattcctc tgatcaagga ggaatctact ttgatcaggg tactgataat      720
ccgaaacagc gctgggcaat caataagtca ttgcctcttc gtcatggtga cgtagtcacc      780
ttcatgaata agtacttcac tcgcagtggg ctgtgctacg atgatggacc ggcaacaaac      840
gtgtactgtc tggacaaacg tgaagacaag tggattttgg aagtggttgg ttaa           894
```

```
<210> SEQ ID NO 2
<211> LENGTH: 903
<212> TYPE: DNA
<213> ORGANISM: Eisenia fetida

<400> SEQUENCE: 2
```

```
atgtcgtcta gagcaggaat cgcagaggga tatgaacaga tagaagtaga tgtggtggca       60
gtatggaaag aaggctacgt ttacgaaaat cggggaagca ccagtgtgga gcagaagatc      120
aaaataacaa aaggcatgag aaatttgaat tcagaaacaa agacattgac ggcttcgcat      180
agtattggtt ctactattag cactggagat ctatttgaaa tagcaaccgt ggatgttagc      240
tacagctact cacatgaaga atcccaagtt agtatgacgg aaactgaagt ttatgaatca      300
aaggaaatcg aacacactat aacgattcca cctacttcaa aattcacaag atggcaactg      360
aatgctgacg ttggtggagc ggatattgaa tacatgtatt tgattgatga agtcacaccc      420
ataggaggga ctctgagtat tccacaggtc atcaaaagtc gggctaaaat tctagttggc      480
cgagaaatat accttggaga aacagaaatt cgaataaagc atgcggacag gaaagagtat      540
atgacagtcg tttcaagaaa aagctggcca gctgcaactc ttggacatag caaactttac      600
aagtttgtgc tctatgaaga tatgtatgga tttcgaatta aaacgctgaa caccatgtat      660
tcgggctatg agtatgccta ttcctctgat caaggaggaa tctactttga tcagggtagt      720
gataatccga acagcgctg ggcaatcaat aagtcattgc ctcttcgtca tggtgacgta      780
gtcaccttca tgaataagta cttcactcgc agtggtctgt gctactatga tggaccggca      840
acagacgtgt actgtttgga caaacgtgaa gacaagtgga ttttagaagt ggttaaaccc      900
taa                                                                    903
```

```
<210> SEQ ID NO 3
<211> LENGTH: 298
<212> TYPE: PRT
<213> ORGANISM: Eisenia fetida

<400> SEQUENCE: 3
```

```
Met Ser Ala Lys Ala Ala Glu Gly Tyr Glu Gln Ile Glu Val Asp Val
 1               5                  10                  15

Val Ala Val Trp Lys Glu Gly Tyr Val Tyr Glu Asn Arg Gly Ser Thr
                20                  25                  30

Ser Val Asp Gln Lys Ile Thr Ile Thr Lys Gly Met Lys Asn Val Asn
            35                  40                  45

Ser Glu Thr Lys Thr Leu Thr Ala Ser His Ser Ile Gly Ser Thr Ile
        50                  55                  60
```

-continued

| | | | | | | | | | | | | | | |
|---|---|---|---|---|---|---|---|---|---|---|---|---|---|---|
|Ser|Thr|Gly|Asp|Leu|Phe|Glu|Ile|Ala|Thr|Val|Asp|Val|Ser|Tyr|Ser|
|65| | | |70| | | |75| | | |80| | |

Tyr Ser His Glu Glu Ser Gln Val Ser Met Thr Glu Thr Glu Val Tyr
            85                 90             95

Glu Ser Lys Glu Ile Glu His Thr Ile Thr Ile Pro Pro Thr Ser Lys
          100              105            110

Phe Thr Arg Trp Gln Leu Asn Ala Asp Val Gly Gly Ala Asp Ile Glu
        115             120             125

Tyr Met Tyr Leu Ile Asp Glu Val Thr Pro Ile Glu Gly Thr Leu Ser
   130             135            140

Ile Pro Gln Val Ile Lys Ser Arg Ala Lys Ile Leu Val Gly Arg Glu
145            150            155          160

Ile Tyr Leu Gly Glu Thr Glu Ile Arg Ile Lys His Ala Asp Arg Lys
        165             170             175

Glu Tyr Met Thr Val Val Ser Arg Lys Ser Trp Pro Ala Ala Thr Leu
          180              185            190

Gly His Ser Lys Leu Tyr Lys Phe Val Leu Tyr Glu Asp Met Tyr Gly
       195            200            205

Phe Arg Ile Lys Thr Leu Asn Thr Met Tyr Ser Gly Tyr Glu Tyr Ala
   210             215            220

Tyr Ser Ser Asp Gln Gly Gly Ile Tyr Phe Asp Gln Gly Ser Asp Asn
225            230            235          240

Pro Lys Gln Arg Trp Ala Ile Asn Lys Ser Leu Pro Leu Arg His Gly
        245             250             255

Asp Val Val Thr Phe Met Asn Lys Tyr Phe Thr Arg Ser Gly Leu Cys
          260              265            270

Tyr Tyr Asp Gly Pro Ala Thr Asp Val Tyr Cys Leu Asp Lys Arg Glu
   275             280            285

Asp Lys Trp Ile Leu Glu Val Val Lys Pro
   290             295

<210> SEQ ID NO 4
<211> LENGTH: 894
<212> TYPE: DNA
<213> ORGANISM: Eisenia fetida

<400> SEQUENCE: 4

```
atgtcggcta aagcagcaga gggatatgaa cagatagaag tagatgtggt ggcagtatgg      60
aaagaaggct atgtatacga aaatcgcgga agcaccagtg tggatcagaa gatcacaata     120
acaaaaggca tgaaaaatgt gaattcagaa acaaagacat tgacggcttc gcatagtatt     180
ggttctacta ttagcactgg agatctattt gaaatagcaa ccgtggatgt tagctacagc     240
tactcacatg aagaatccca agttagtatg acggaaactg aagtttatga atcaaaggaa     300
atcgaacaca ctataacgat tccacctact tcaaaattca agatggcaa actgaatgct     360
gacgttggtg gagcggatat tgaatacatg tatttgattg atgaagtcac acccatagga     420
gggactctga gtattccaca ggtcatcaaa agtcgggcta aaattctagt tggccgagaa     480
atataccttg agaaacagaa attcgaata aagcatgcgg acaggaaaga gtatatgaca     540
gtcgtttcaa gaaaagctg gccagctgca actcttggac atagcaaact ttacaagttt     600
gtgctctatg aagatatgta tggatttcga attaaaacgc tgaacaccat gtattcgggc     660
tatgagtatg cctattcctc tgatcaagga ggaatctact ttgatcaggg tagtgataat     720
ccgaaacagc gctgggcaat caataagtca ttgcctcttc gtcatggtga cgtagtcacc     780
```

-continued

```
ttcatgaata agtacttcac tcgcagtggt ctgtgctact atgatggacc ggcaacagac     840
gtgtactgtt tggacaaacg tgaagacaag tggattttag aagtggttaa accc           894
```

<210> SEQ ID NO 5
<211> LENGTH: 180
<212> TYPE: PRT
<213> ORGANISM: Eisenia fetida

<400> SEQUENCE: 5

```
Leu Asn Ala Asp Val Gly Gly Ala Asp Ile Glu Tyr Met Tyr Leu Ile
1               5                   10                  15

Asp Glu Val Thr Pro Ile Gly Gly Thr Gln Ser Ile Pro Glu Val Ile
            20                  25                  30

Thr Ser Arg Ala Lys Ile Ile Val Gly Arg Gln Ile Ile Leu Gly Lys
        35                  40                  45

Thr Glu Ile Arg Ile Lys His Ala Glu Arg Lys Glu Tyr Met Thr Val
    50                  55                  60

Val Ser Arg Lys Ser Trp Pro Ala Ala Thr Leu Gly His Ser Lys Leu
65                  70                  75                  80

Phe Lys Phe Val Leu Tyr Glu Asp Trp Gly Gly Phe Arg Ile Lys Thr
                85                  90                  95

Leu Asn Thr Met Tyr Ser Gly Tyr Glu Tyr Ala Tyr Ser Ser Asp Gln
            100                 105                 110

Gly Gly Ile Tyr Phe Asp Gln Gly Thr Asp Asn Pro Lys Gln Arg Trp
        115                 120                 125

Ala Ile Asn Lys Ser Leu Pro Leu Arg His Gly Asp Val Val Thr Phe
    130                 135                 140

Met Asn Lys Tyr Phe Thr Arg Ser Gly Leu Cys Tyr Asp Asp Gly Pro
145                 150                 155                 160

Ala Thr Asn Val Tyr Cys Leu Asp Lys Arg Glu Asp Lys Trp Ile Leu
                165                 170                 175

Glu Val Val Gly
            180
```

<210> SEQ ID NO 6
<211> LENGTH: 543
<212> TYPE: DNA
<213> ORGANISM: Eisenia fetida

<400> SEQUENCE: 6

```
ctgaatgctg acgttggtgg agcggatatt gaatacatgt atttgattga tgaagtcaca     60
cccataggag ggactcagag tattccacag gtcatcacaa gtcggctaa aattatagtt     120 ggccgacaga taatccttgg aaaaacagaa attcgaatta agcatgcaga aggaaggag     180 tacatgacag tcgtttcaag aaaaagttgg ccagctgcaa ctcttggaca tagcaaactt    240
ttcaagtttg tgctctatga agattggggg ggatttcgaa ttaaaacgct gaacaccatg    300
tattcgggct atgagtatgc ctattcctct gatcaaggag gaatctactt tgatcagggt    360
actgataatc cgaaacagcg ctgggcaatc aataagtcat tgcctcttcg tcatggtgac    420
gtagtcacct tcatgaataa gtacttcact cgcagtgggc tgtgctacga tgatggaccg    480
gcaacaaacg tgtactgtct ggacaaacgt gaagacaagt ggattttgga agtggttggt    540
taa                                                                  543
```

```
<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
ttcggatcca tgtcggctaa agcagca                                27

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
aagcttccgc tttagttgca cctcatc                                27

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
ttcggatcca tgtcgtctag agcagga                                27

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
aagcttaaaa catgcggaag caaatgt                                27

<210> SEQ ID NO 11
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: n
<222> LOCATION: (16)..(20)
<223> OTHER INFORMATION: n is any base

<400> SEQUENCE: 11
ttcggatccc tgaatgntga cgttggtgga                             30

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
aagcttccgc tttagttgca cctcatc                                27
```